US00PP32760P2

(12) United States Plant Patent
Marques

(10) Patent No.: US PP32,760 P2
(45) Date of Patent: Jan. 19, 2021

(54) ***HYDRANGEA* PLANT NAMED 'HSOPR015'**

(50) Latin Name: *Hydrangea serrata*
Varietal Denomination: HSOPR015

(71) Applicant: Wouter Marques, Rijkevorsel (BE)

(72) Inventor: Wouter Marques, Rijkevorsel (BE)

(73) Assignee: OPRINS PLANT N.V., Rijkevorsel (BE)

( * ) Notice: Subject to any disclaimer, the term of this patent is extended or adjusted under 35 U.S.C. 154(b) by 0 days.

(21) Appl. No.: 16/873,702

(22) Filed: Jun. 2, 2020

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48; A01H 5/02
See application file for complete search history.

*Primary Examiner* — Keith O. Robinson
(74) *Attorney, Agent, or Firm* — Penny J. Aguirre

(57) ABSTRACT

A new cultivar of *Hydrangea serrata* plant named 'HSOPR015' that is characterized by its a plant habit that is low growing and almost ground covering, its suckering roots, its red-purple fall foliage coloration, and its inflorescences that are held primarily above the foliar plane.

2 Drawing Sheets

Botanical classification: *Hydrangea serrata.*
Varietal denomination: 'HSOPR015'.

CROSS REFERENCE TO A RELATED APPLICATION

This application is related to a European plant breeders' rights application filed on Oct. 24, 2017, application No. 2017/2689. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Hydrangea serrata* and will be referred to hereafter by its cultivar name, 'HSOPR015'. 'HSOPR015' represents a new *Hydrangea*, a perennial shrub grown for landscape use and as a potted plant.

'HSOPR015' was derived from a breeding program conducted by the Inventor at his nursery in Merksplas, Belgium. The objective of the breeding program is to select new cultivars of *Hydrangea* with low growing plant habits and long blooming habits.

'HSOPR015' arose from controlled cross made in July of 2010 between an unnamed and unpatented plant of *Hydrangea serrata* var. *yesoensis* as the female patent and an unnamed and unpatented plant of *Hydrangea serrata* as the male parent. 'HSOPR015' was selected a single unique plant from the above cross in August of 2014.

Asexual propagation of the new cultivar was first accomplished by softwood stem cuttings by the Inventor in September of 2015 in Merksplas, Belgium. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'HSOPR015' as a unique cultivar of *Hydrangea.*

1. 'HSOPR015' exhibits a plant habit that is low growing and almost ground covering.
2. 'HSOPR015' exhibits suckering roots.
3. 'HSOPR015' exhibits red-purple fall foliage coloration.
4. 'HSOPR015' exhibits a prolific blooming habit regardless if pruned in fall or early spring.
5. 'HSOPR015' exhibits inflorescences that are held primarily above the foliar plane.

The female parent of 'HSOPR015' differs from 'HSOPR015' in having a much taller plant height and an upright growth habit. The male parent of 'HSOPR015' differs from 'HSOPR015' in having inflorescences that are held within the foliage. 'HSOPR015' can be most closely compared to the *Hydrangea serrata* cultivars 'Spreading Beauty' (not patented) and 'Kurenai' (not patented). 'Spreading Beauty' is similar to 'HSOPR015' in having a compact plant shape, inflorescences with sterile and fertile flowers with fertile flowers being clearly visible and in having a similar inflorescence coloration. 'Spreading Beauty' differs from 'HSOPR015' in having more conspicuously serrated leaf margins and in not producing root suckers. 'Kurenai' is similar to 'HSOPR015' in having inflorescences with sterile and fertile flowers with fertile flowers being clearly visible and in having a similar inflorescence coloration. 'Kurenai' differs from 'HSOPR015' in not producing root suckers, in having a less compact plant habit, and in commencing bloom later in the season.

BRIEF DESCRIPTION OF THE DRAWINGS

The accompanying colored photographs illustrate the overall appearance and distinct characteristics of the new

*Hydrangea*. The photographs were taken of a two-year-old plant of 'HSOPR015' as field grown in Stroe, The Netherlands and placed in a 25-cm container for the photographs.

Figure 1:
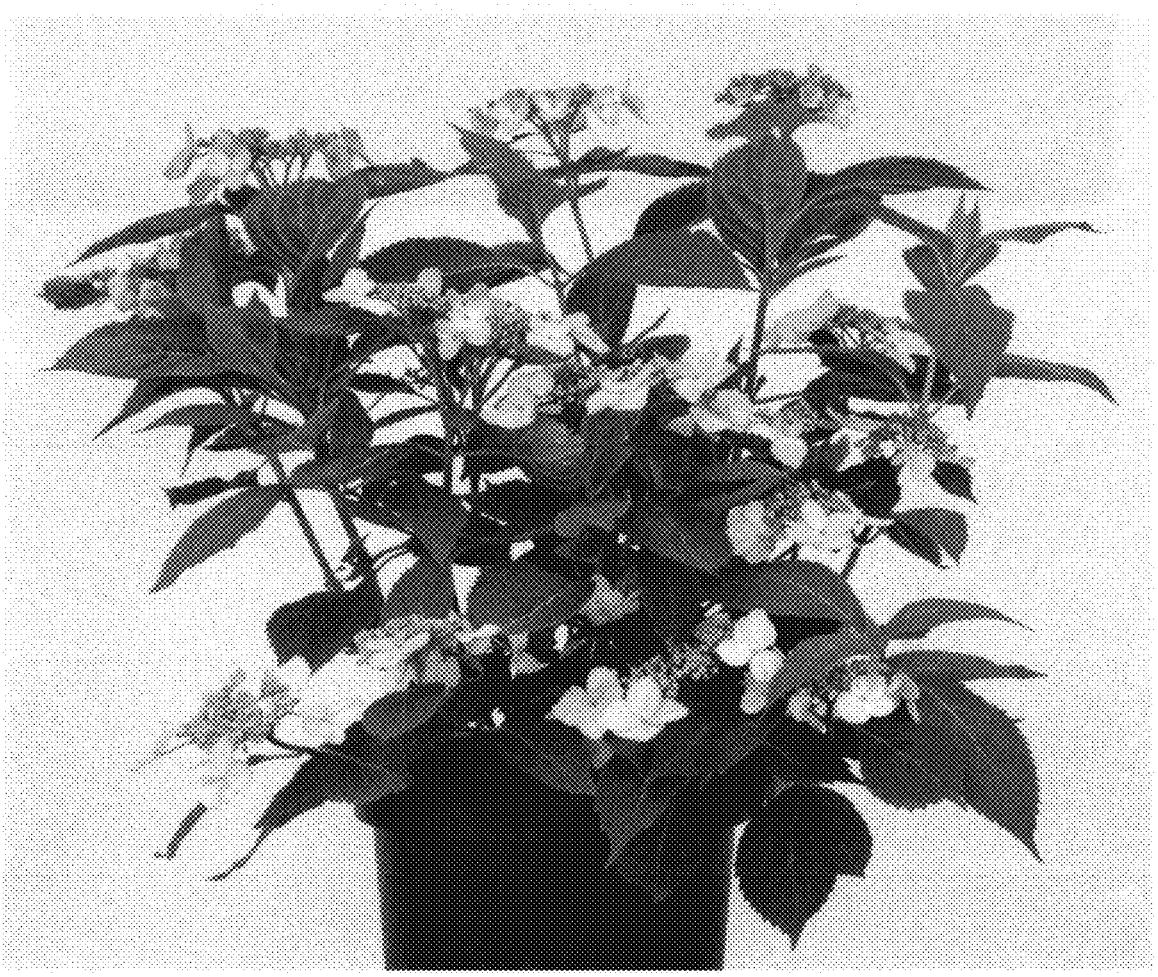

The photograph in FIG. 1 provides a side view of the plant habit of 'HSOPR015' in bloom.

Figure 2:
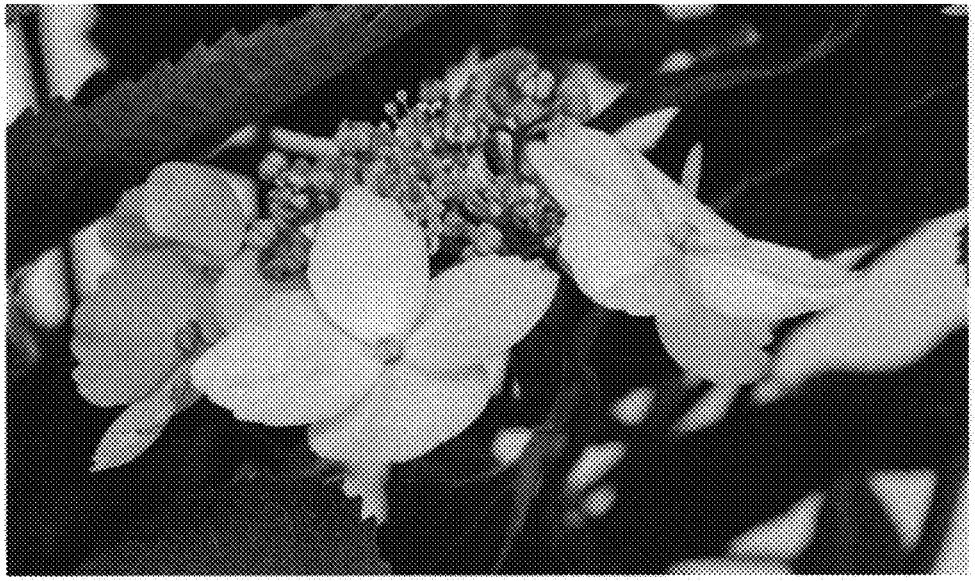

The photograph in FIG. 2 provides a close-up view of an inflorescence of 'HSOPR015'.

Figure 3:
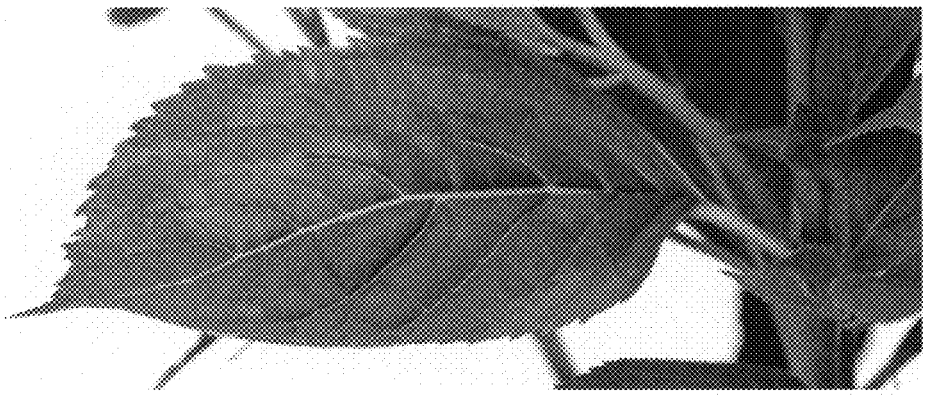

The photograph in FIG. 3 provides a close-up view of a leaf of 'HSOPR015'.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of two-year-old plants of 'HSOPR015' as field grown in Stroe, The Netherlands and placed in 25-cm containers for the photographs. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Approximately 6 weeks from May to late June in The Netherlands.

*Plant type*.—Deciduous shrub.

*Plant habit*.—Low growing and spreading upright, nearly groundcover-like.

*Height and spread*.—Reaches 44 cm in height and 59.8 cm in spread as grown in a 25-cm container, reached about 50 cm in height and 150 cm in width in the landscape.

*Cold hardiness*.—At least in U.S.D.A. Zone 6.

*Diseases and pests*.—No susceptibility and resistance to diseases or pests has been observed.

*Root description*.—Fine, fibrous and dense, NN155A and 164A in color.

*Propagation*.—Softwood stem cuttings.

*Root development*.—An average of 70 days for root initiation with a young rooted plant produced in an average of 5 months.

*Growth rate and vigor*.—Moderate.

Stem description:

*Stem shape*.—Rounded.

*Stem strength*.—Strong.

*Stem color*.—Young; 144B, mature; between 144A and 146B, internodes N186C, bark 199C to 200C.

*Stem size*.—Average of 31.5 cm in length and 5 mm in diameter.

*Stem surface*.—Young stems have 2 shallow wings; average of 1 mm in length, rounded when maturing, stem and wings are glabrous.

*Stem aspect*.—Upright, average angle of 55° to soil level.

*Internode length*.—An average of 6.6 cm.

*Branching*.—Freely branched from the base with an average of 24 lateral branches.

Foliage description:

*Leaf shape*.—Broadly ovate to nearly elliptic.

*Leaf arrangement*.—Opposite.

*Leaf division*.—Simple.

*Leaf base*.—Attenuate.

*Leaf apex*.—Apiculate.

*Leaf margins*.—Serrate.

*Leaf venation*.—Pinnate, color; upper surface 144B, lower surface 145A to 145B.

*Leaf size*.—An average of 11.7 cm in length and 7 cm in width.

*Leaf attachment*.—Petiolate.

*Leaf number*.—An average of 12 per lateral stem.

*Leaf surface*.—Upper surface slightly rugose, rough to the touch, densely covered with very short strigose hairs, 0.75 mm, 155A in color, lower surface slightly rugose, sparsely to moderately covered with very short hairs; an average of 0.3 mm in length and too small to measure color.

*Leaf color*.—Young upper surface; 143A, young lower surface; between 138A and 146B, mature upper surface; between NN137A and 147A, mature lower surface; 147B, fall on upper and lower surface; a blend of 58A and 58B.

*Petioles*.—Average of 3 cm in length, 4 mm in diameter, glabrous and slightly glossy surfaces, upper surface color 146C, margins 182A, lower surface 144B, margins 182A.

Inflorescence description:

*Inflorescence type*.—Flattened, typical lace-cap, comprised of central fertile flowers, margined by sterile flowers.

*Lastingness of inflorescence*.—Sterile flowers; persistent for an average of 6 weeks, fertile flowers; self-cleaning, an average of 5 days.

*Inflorescence number*.—One per lateral stem.

*Inflorescence size*.—An average of 8 cm in height and 13.9 cm in diameter.

*Flower number*.—An average of 7 sterile flowers and 380 fertile flowers.

*Flower fragrance*.—Moderately strong, somewhat moldy fragrance.

*Flower aspect*.—Sterile flowers; upright, outward to slightly drooping when fading, fertile flowers; held upright.

*Flower size*.—Sterile flowers; up to 4.4 cm in diameter and 9 mm in depth, fertile flowers; an average of 1 cm in diameter and 1 mm in depth.

*Flower type*.—Sterile flowers rotate, fertile flowers rotate with petals drop when mature.

*Flower buds*.—Sterile flowers; an average of 9 mm in length and 2 cm in diameter, bowl-shaped, color; 145B, changing to 144B at the base, 67D at the top, fertile flowers; an average of 5 mm in length and 3 mm in diameter, obovate in shape, color; 160C, moderately tinged 75B, changing fully to 75B at the base, 72C to 72D at the top.

*Peduncles*.—Primary peduncles; strong, flattened oval in shape, an average of 2.5 cm in length and 3 mm in width. secondary peduncles 1 cm in length and 2 mm in width, color 146D and tinged with a color between 75C to 75D, surface moderately covered with a thin pubescence; average of 0.2 mm in length and too small to measure color.

*Pedicels*.—Sterile flowers; moderate strength, an average of 2.1 cm in length and 1.25 mm in width, a color between 75C to 75D held in an average angle of 25°, surface is matte, moderately covered with thin pubescence; average of 0.2 mm in length and too small to measure color, fertile flowers; moderate strength, an average of 2 mm in length, 1 mm in diameter, held in an average angle of 20°, a color between 75C to 75D, surface is matte and glabrous.

*Petals*.—Sterile flowers; average of 4, rotate, ovate to concave in shape, acute apex, cuneate base, entire margins, 3 mm in length, 1.5 mm in width, both surfaces glabrous, matte, color when opening and fully open upper surface 77C, changing to 91A, color when opening and fully open lower surface 76C, tinged 160C, 91A at the base, fertile flowers; average of 5, rotate, ovate to concave in shape, acute apex, cuneate base, entire margins, 4 mm in length and 1.8 mm in width, both surfaces are glabrous and matte, color when opening and fully open upper surface 77C, changing to 91A at the base, color when opening and fully open lower surface 76C, tinged 160C, tinged 160C, 91A at the base.

*Sepals*.—Sterile flowers; 4 (occasionally 3 to 5), rotate, broadly ovate to reniform to orbicular in shape, apex is obtuse to broadly, bluntly acute, base is broadly cuneate, margins are crenate to serrate with blunt teeth, non-undulate, 2.5 cm in length, 2.4 cm in width, both surfaces glabrous and matte, color; when opening upper surface 75A to 75B, occasionally tinged 91B, occasionally veined 91A, when opening lower surface 75B to 75D, occasionally changing to N75C at the top, changing to 145C at the base, when fully open upper surface 72D and 73A, veins tinged 92B, when fully open lower surface 75B, veins 145A to 145B, upper surface changing to 144B, slightly to strongly tinged towards the tip 172A to 172B, lower surface fading to 176B, fertile flowers; average of 5, rotate, short deltoid in shape, broadly acute apex, broadly cuneate base, entire margins, 1.75 mm in length, 1 mm in width, both surfaces glabrous and matte, color; when opening and fully opening upper and lower surface 146D.

Reproductive organs:

*Gynoecium*.—Sterile flowers; 2 pistils, average of 1 mm in length, stigma is club-shaped, N187D, style 0.6 mm in length, 84A in color, ovary 84A in color, fertile flowers; 4 pistils, an average of 2 mm in length, stigma; club-shaped and 155C in color, style; 1.25 mm in length, NN74D in color, ovary is 75C in color.

*Androecium*.—Sterile flowers; an average of 8 stamens, filaments; an average of 4 mm in length and 85C in color, anthers; double broad oblong in shape, an average of 0.8 mm in length and N187D in color, pollen; moderate to high in quantity and 155A in color, fertile flowers; an average of 10 stamens, filaments; an average of 7 mm in length and N75D in color, changing to 92B at the distil end in color, anthers; double broadly oblong in shape, an average of 0.8 mm in length and N187D in color, pollen; moderate to high in quantity and 155A in color.

*Fruit and seed*.—None observed to date.

It is claimed:

1. A new and distinct cultivar of *Hydrangea* plant named 'HSOPR015' substantially as herein illustrated and described.

* * * * *